United States Patent
Haese

[11] Patent Number: 6,132,138
[45] Date of Patent: Oct. 17, 2000

[54] GRAY WATER RECYCLING SYSTEM

[76] Inventor: Larry Wayne Haese, 8641 Barn Owl La., San Antonio, Tex. 78255

[21] Appl. No.: 08/957,528

[22] Filed: Oct. 24, 1997

[51] Int. Cl.[7] .................................................. F02B 13/00
[52] U.S. Cl. .............................. 405/37; 405/36; 210/167; 210/257.1
[58] Field of Search ................... 405/36, 37, 128, 405/129; 210/767, 257.1, 348, 167

[56] References Cited

U.S. PATENT DOCUMENTS

| | | | |
|---|---|---|---|
| 4,162,218 | 7/1979 | McCormick | 210/167 |
| 4,726,144 | 2/1988 | Young et al. | 405/36 |
| 4,878,781 | 11/1989 | Gregory et al. | 405/36 |
| 4,879,852 | 11/1989 | Tripp | 405/37 |
| 5,059,330 | 10/1991 | Burkhardt | 210/754 |
| 5,106,493 | 4/1992 | McIntosh | 210/167 |
| 5,156,494 | 10/1992 | Owens et al. | 405/36 |
| 5,160,606 | 11/1992 | De Simone | |
| 5,173,180 | 12/1992 | Stewart et al. | 210/167 |
| 5,192,426 | 3/1993 | De Coster | |
| 5,200,065 | 4/1993 | Sinclair et al. | 405/37 |
| 5,217,323 | 6/1993 | Bilson | 405/36 |
| 5,227,068 | 7/1993 | Runyon | |
| 5,288,412 | 2/1994 | Voorhees et al. | 210/257.1 |
| 5,409,616 | 4/1995 | Garbutt et al. | |
| 5,452,956 | 9/1995 | Gilliam | |
| 5,498,330 | 3/1996 | Delle Cave | 210/167 |
| 5,590,980 | 1/1997 | Daniel | |

Primary Examiner—David Bagnell
Assistant Examiner—Frederick L. Lagman
Attorney, Agent, or Firm—Jackson Walker LLP

[57] ABSTRACT

This invention relates to a gray water recycling invention that utilizes filtered gray water for maintaining constant moisture levels in building foundations and for other irrigation uses. The invention allows for the mixture of pesticides with a gray water stream injected under a building in order to treat for insects. Additionally, pesticides, fungicides, or fertilizers can be injected into a gray water stream prior to its application in landscape irrigating. The invention has applications in both a single residence and fill development real estate setting.

14 Claims, 2 Drawing Sheets

GRAY WATER RECYCLING SYSTEM

TECHNICAL FIELD OF THE INVENTION

The field of this invention relates to a method and apparatus for recycling gray water by using the gray water to stabilize building foundations, irrigate landscape, and as a medium for treating residential and landscape insects and fertilizing landscapes.

BACKGROUND OF THE INVENTION

Severe water shortages have become an increasing occurrence, particularly in the southwest and western states of the United States, and a hindrance to the development of commercial and residential properties. An unrelated problem with the use of slab building foundations, a very common building technique involving securing a residence or other structure on top of a horizontal slab of reinforced concrete, is the damage caused to the foundation and the supported structure by expanding and contracting subsoil due to variations in the subsoil moisture content throughout the year. Insect infestations are also the scourge of property owners, particularly in the southern states, and range from termite invasion of wooden above-ground structures by way of nests located in the subsurface below the structure to grub worm and fire ant infestations in lawns. Lawn diseases such as brown patch can also wreak havoc on landscapes if left untreated. All of these seemingly unrelated problems are addressed and managed by the gray water recycling system of the present invention. In fact, in many communities facing severe water shortages the use of potable water to stabilize building foundations and irrigate landscapes is prohibited or severely restricted. However, a gray water recycling system would not be subject to such water control programs.

The present invention permits the recycling of gray water in various unique applications with resulting diverse benefits. By way of explanation, effluent discharged from a residence is typically classified as black water or gray water. Black water refers to water drained from sources likely to include fecal matter, grease, and high levels of bacteria, such as toilets, dishwashers, and garbage disposals. Gray water is effluent obtained from sources not likely to contain grease, fecal matter or other high concentrations of bacteria, such as bathtubs, showers, laundry washers, lavatory sinks, and the condensate drain from air conditioning units. Gray water normally contains small amounts of soap and detergent and is generally safe for reuse in applications where clean, potable water is unnecessary.

Prior art gray water recycling systems typically separate the black water and gray water effluent streams. The black water is directed to a septic tank or other sewage treatment. The gray water is then routed back to residential toilets or used in landscape irrigation, thus saving on costs associated with treating the water to a potable state and avoiding the need for obtaining potable water from other sources.

The present invention involves recycling gray water in order to obtain substantially more benefits than merely watering landscape or use in residential toilets. One aspect of the present invention involves the use of the gray water effluent along with a foundation irrigation system to maintain a constant subsoil moisture level in expansive soil. This aspect of the invention protects slab foundations in expansive soil from shifting and cracking, therefore maintaining the integrity of the supported structure. The present invention incorporates an external fluid injection capability into the foundation irrigation stream that also allows for the introduction of pesticides into the subsoil under the slab foundation. This aspect of the invention is ideal for the treatment of termites and other subsoil insect infestations and eliminates the need for the present costly methods of treating for such insects in similar structures by drilling vertically through the foundation and injecting chemicals into the subsoil. The present invention also allows for additives to a gray water stream prior to use of the gray water for landscape irrigation purposes. This additive could be a fertilizer, fungicide, or a pesticide, depending on the application required.

The incorporation and all of these benefits of the present invention can occur in either a micro application for an individual residence or a macro application for an entire development.

As will be described in more detail below, the gray water recycling system invention disclosed allows for a flexible and varied approach to several problems facing property owners and managers while additionally promoting the recycling of a scarce natural resource.

SUMMARY OF INVENTION

This invention relates to a gray water recycling system which helps conserve water while using the gray water effluent in several beneficial applications in the single residence, residential development, and commercial real estate context. The invention involves filtering gray water from gray water sources, collecting the filtered gray water, pressurizing the filtered gray water, and introducing the pressurized and filtered gray water in several applications integral to the invention. One of these applications is the maintenance of constant subsoil moisture levels in expansive soil supporting foundations. The invention allows for the injection of a pesticide in the same application for a simple and practical method for treating subsoil insect infestations, such as termite nests. Another application for the filtered gray water is for landscape irrigation. The capability of the invention for the injection of pesticides into the gray water also allows for the application of pesticides concurrent with the invention's landscape irrigation features. Likewise, water-soluble fertilizers or fungicides can be added to the gray water prior to its use in landscape irrigation. The gray water invention disclosed is practical in both single residential applications as well as large development or commercial applications.

Critical goals of the invention include conservation of water (an increasingly scarce resource), the reduction of water treatment expenses, the stabilization of building foundations in areas susceptible to wide variations in subsoil compaction due to changing moisture levels in the subsoil, landscape irrigation with the capability of injecting water-soluble insecticides, fungicides, and/or fertilizers into the irrigation water, and a simple and effective method for the treatment of subsoil insects under building foundations, such as termites. The present invention accomplishes all of these goals with a simple construction and a cost efficient and low maintenance design.

The invention collects gray water from gray water sources, such as residential bathtub drains, lavatory sink drains, air conditioning unit condensate drains, and drains for laundry washing machines. This gray water source is routed through a filter to remove particles, soap scum, and other solids. Filtered gray water is then stored in a collection tank. The available gray water for the applications described below can be augmented by a potable water source. This potable water source is used to maintain a constant minimum level in the gray water holding tank.

From the holding tank, the gray water is pressurized by way of a water pump. After pressurization, a portion of the gray water stream can be diverted through a venturi injection meter for the injection of water-soluble additives to the gray water stream. These additives might include pesticides, fungicides, or fertilizers. Gray water can then be routed to a landscape irrigation system. In addition, the pressurized gray water can be routed to a foundation watering system. In a typical residential setting, this foundation watering system involves the placement of osmosis irrigation piping underneath the foundation. The point of discharge for the irrigation piping is such that equal distribution of the irrigation fluids migrate simultaneously towards the center of the foundation and to the outward edges of the foundation, without allowing for significant migration of the fluid beyond the edges of the foundation. Moisture probes located near the center and edges of the foundation subsoil ensure the distribution of the fluid to that point. The ability to inject additives into the pressurized gray water stream prior to watering the foundation allows for a simple method for treating for termites and other subsoil insects. The arrangement of the osmosis irrigation piping allows for a uniform coverage of the entire subsoil below the foundation without migration of the pesticide beyond the foundation.

The present invention is a substantial improvement over the prior art in providing for several beneficial uses of gray water in the recycling context in a system that is simple in design, efficient, and easily maintained.

BRIEF DESCRIPTION OF THE DRAWINGS

Further objects and advantages of the present invention will become apparent through the following detailed description when read in conjunction with the accompanying drawings, in which.

DETAILED DESCRIPTION OF PREFERRED EMBODIMENT

Figure 1:
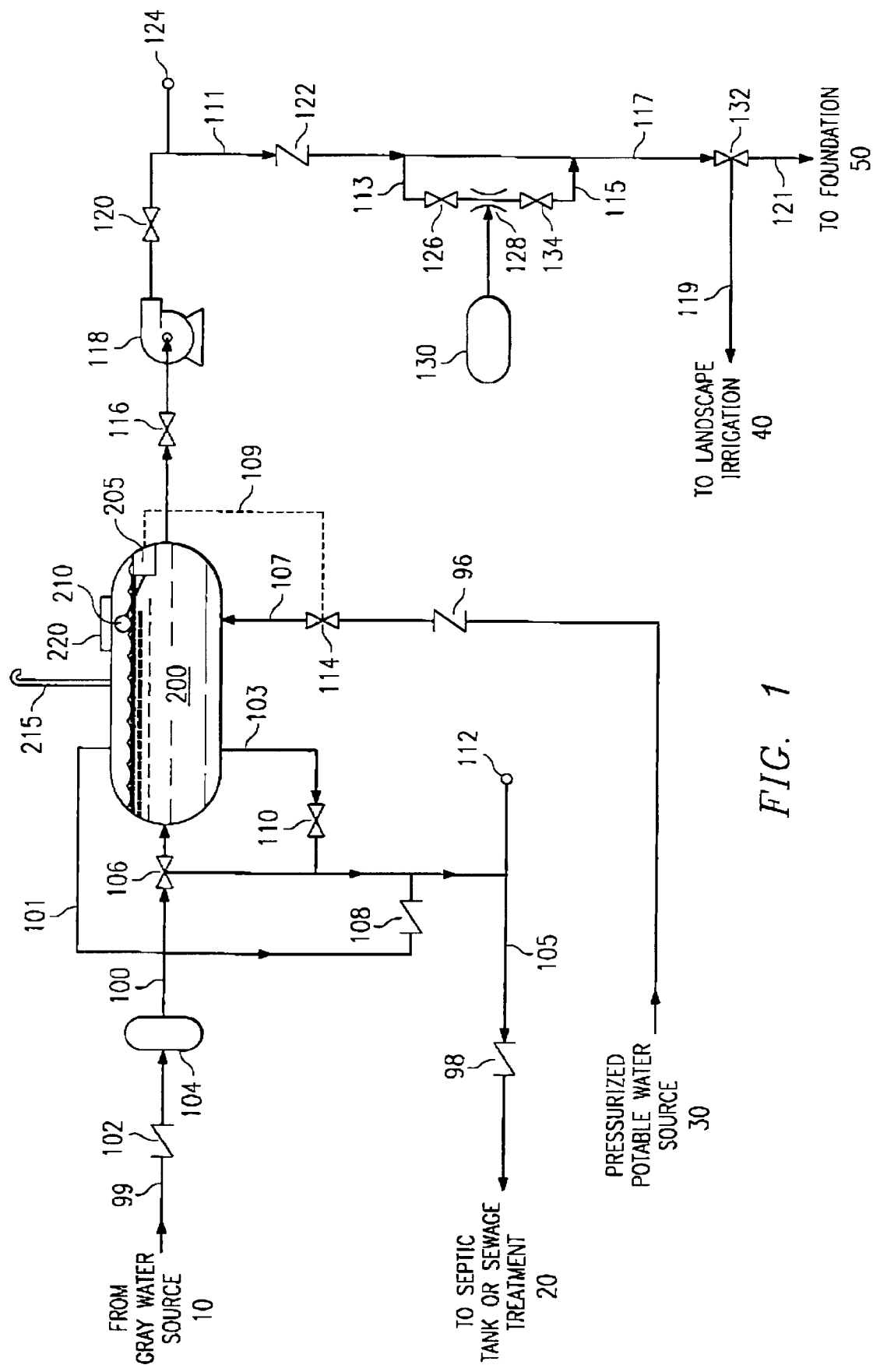
FIG. 1 is a schematic drawing of the single residence embodiment of the present invention.

FIG. 1 is a schematic drawing of the single residence embodiment of the present invention. Gray water enters the system from a gray water source 10, such as the accumulated effluent from the shower drain, bathtub drain, bathroom sink drains, laundry washing machine drain, and air conditioning unit condensate drain. This raw and unfiltered gray water stream 99 passes first through a one-way check valve 102 which prevents back flow of the gray water to the original gray water source 10. The raw gray water stream 99 then passes through a filter 104 for the removal of particulate matter, soap scum, and other solids. The filtered gray water stream then passes through a three-way diverter valve 106. In a first position, the diverter valve 106 directs the filtered gray water stream 100 to a holding tank 200. In a second position, the diverter valve 106 directs the filtered gray water stream 100 to a discharge stream 105, which ultimately flows to a septic tank or sewage treatment facility 20. In a third position, the diverter valve 106 closes both gray water stream 100 and discharge stream 105, therefore isolating the holding tank 200 from these two streams.

Turning to the operation of the holding tank 200, it is expected that the gray water source 10 will provide varying quantities of effluent at times that may not be consistent with the later described uses for the gray water. Consequently, it is desirable to maintain the holding tank 200 volume within certain prescribed levels. This is accomplished in the embodiment depicted by use of a tank level monitor 205 connected to a tank level float 210. When the fluid level in the tank falls below a predetermined minimum level the tank level monitor 205 signals a solenoid valve 114 by way of an electrical signal 109 to allow for the introduction of a pressurized potable water stream 107 from a pressurized potable water source 30, such as a municipal water main. A syphon breaker, air gap fitting, or one-way check valve 96 is installed prior to the solenoid valve 114 in order to prevent back flow into the potable water source. The holding tank 200 is also constructed with an overflow outlet line 101 at the top of the tank in order to preclude over pressurization of the tank 200 and upstream back pressure of the filtered gray water stream 100. The overflow discharge from holding tank 200 precedes through a one-way check valve 108 to prevent back flow from the discharge stream 105 reentering the tank 200. The holding tank 200 also has a tank drain line 103 controlled by a valve 110 which allows fluid to drain from the holding tank 200 into the discharge stream 105. The discharge stream 105 passes through a one-way check valve 98 in order to prevent back flow from the septic tank or sewage treatment facility 20. The discharge stream 105 is accessible through a clean out access 112.

Other features of the holding tank 200 include a tank vent 215 and a tank access hatch 220. The holding tank 200 is typically buried underground. The tank vent 215 allows for atmospheric venting of the holding tank 200 and is typically routed through and protrudes above the roof of the residence. The tank access hatch 220 is accessible at ground level and allows for access to the holding tank 200 for the purposes of cleaning the tank 200 and conducting maintenance or inspection functions on the tank level monitor 205.

By opening valve 116, gray water flows out from the holding tank 200 into a pump 118. This pump 118 pressurizes the gray water, and this pressurized gray water stream 111 then passes through a valve 120 and a one-way check valve 122. The one-way check valve 122 prevents back flow from the downstream irrigation functions described below. Upstream of the one-way check valve 122 is a clean out access 124. A portion of the pressurized and filtered gray water stream 111 is diverted at a point downstream of the one-way check valve 122. The flow rate on this diverted stream 113 is controlled by valve 126. The diverted stream 113 passes through valve 126 and then flows through a venturi injection meter 128. This venturi injection meter 128 constricts the flow of the diverted stream 113 and allows for the injection of water-soluble pesticides, fungicides, or fertilizers contained in an injection fluid vessel 130. These water-soluble additives are drawn into the diverted stream 113 by virtue of the venturi effect created by the constriction of the venturi injection meter 128. This injected stream 115 is then reintroduced into the gray water output stream 117 passing through valve 134. The venturi injection meter 128 can be isolated, and the diverted stream 113 completely closed, by closing both valve 126 and valve 134.

This gray water output stream 117, with its mixture of fertilizer, fungicide, or pesticide, can then be routed to a number of beneficial aqueous applications which do not require potable water. In fact, in many communities potable water is not permitted for landscape and foundation watering. As shown in FIG. 1, a gray water stream 117 can be directed by a two-way diverter valve 132 to either a landscape irrigation stream 119 for the purpose of irrigating various types of landscape through a landscape irrigation system 40, or a foundation watering stream 121 which might be directed back to the foundation 50 of the residence from which the gray water source 10 was originally collected. The landscape irrigation system 40 could be an above-ground sprinkler system, a below-ground osmosis system, or any combination thereof. It should be noted that local ordinances or codes may require a strictly underground irrigation system The landscape irrigation system 40 could be activated manually or automatically through electronic timers or moisture sensors. The injection of fertilizers, fungicides, or pesticide into the gray water stream 119 allows for a flexible application of water-soluble chemicals for the treatment of various landscape conditions.

Figure 2:
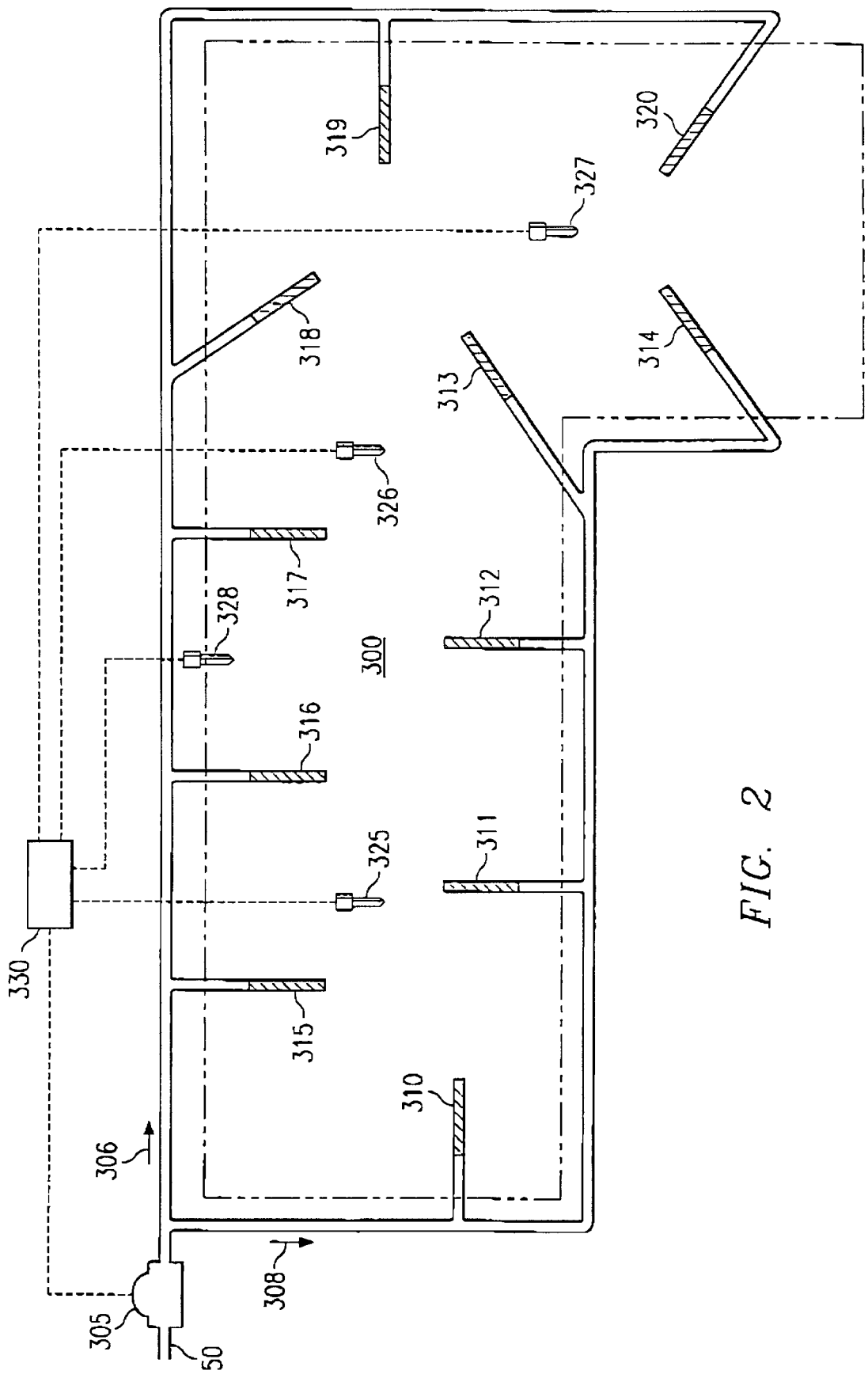
FIG. 2 is an overhead view of a piping diagram illustrating the subsurface irrigation of a slab foundation.

The foundation watering portion of the present invention is further described in FIG. 2, which depicts an overhead view of a piping diagram illustrating the subsurface irrigation of a slab foundation 300. The gray water recycled by the embodiment described in FIG. 1 is first routed through a solenoid valve 305. This solenoid valve is controlled by a moisture monitoring device 330. The moisture monitoring device collects data on the moisture level of the subsoil under and around the slab by use of one or more moisture sensing probes 325, 326, 327, 328. These probes 325, 326, 327, 328 could be simple wet/dry probes or probes that detect the percentage of moisture found in the subsoil under and around the foundation 300. The moisture monitor 330 collects and processes the data from the moisture probes 325, 326, 327, 328 and opens the solenoid valve 305 to allow for the introduction of gray water into the foundation watering system when the moisture level under the foundation slab 300 falls below a predetermined level. The moisture monitor 330 could also simultaneously start pump 118 depicted in FIG. 1, thus pressurizing the gray water stream 121.

As shown in the embodiment depicted in FIG. 2, the gray water is then diverted into two separate streams 306, 308 which run below the surface around the edge of the slab foundation 300. The gray water then flows into various osmosis irrigation outlets 310, 311, 312, 313, 314, 315, 316, 317, 318, 319, 320. Said osmosis irrigation outlets are arranged to allow for the seepage of gray water from the depicted piping system into pre-determined zones under the slab foundation 300. The arrangement of the zones, and the placement of the osmosis irrigation outlets, is such that concentration gradients drive the gray water fluid, and any pesticide that might be mixed therewith, towards the center and outer edges of the slab foundation 300. Ideally, the moisture level by virtue of the placement of these osmosis irrigation outlets, should remain relatively constant throughout the subsoil found immediately below the foundation slab 300 with minimal migration of the gray water beyond the outer edges of the slab foundation 300.

The combination of the capability to inject pesticides into the gray water stream depicted in FIG. 1 along with the foundation watering system depicted in FIG. 2 allows for a simply and effective application of pesticides for the treatment of subsoil insects, such as termites. The appropriate arrangement of the osmosis irrigation outlets 310, 311, 312, 313, 314, 315, 316, 317, 318, 319, 320 would allow for the migration of pesticide throughout the subsoil located below the slab foundation 300 without significant migration of the pesticide beyond the outer edges of the slab foundation 300. Such a system is simple, safe and effective, and a vast improvement over the current method for treatment of subsoil insects which involves drilling vertical holes through the foundation slab 300 for the injection of pesticides into the subsoil.

FIGS. 1 and 2 depict the present invention in its embodiment for use in a single resident setting. However, even greater benefit from the present invention is derived from use of this system in larger settings, such as an entire residential development. Rather than directing the gray water to a single small holding tank for each residence, as depicted in FIG. 1, the gray water collected from each gray water source in a larger residential community can be directed to a centralized holding or treatment facility. The gray water from the centralized facility can then be routed back to each residence for use in a foundation watering system such as depicted on FIG. 2 and for landscape irrigation for the adjoining property of the residence. Accordingly, each residence in such residential development would have two water sources, one a potable water source and one a gray water source, and two effluent discharge systems, one a black water discharge to a septic tank or treatment facility and the second a gray water discharge back to the centralized facility. In the development context, the gray water can also be used for irrigating a communal greenbelt landscape or associated golf course, and can be used to stabilize the foundations of non-residential buildings associated with the development.

It should be understood that various changes in the details, materials and arrangements of the systems which have been described and illustrated in order to explain the nature of the invention may be made by those skilled in the art within the principal and scope of the invention as expressed in the following claims.

What is claimed is:

1. A method for recycling gray water comprising the steps of:
   (a) collecting gray water;
   (b) passing said gray water through a filter to remove particles and solids; and
   (c) utilizing said filtered gray water in an aqueous application, wherein said aqueous application can not use black water but does not require potable water, said aqueous application utilizing the gray water to maintain constant moisture levels in the subsoil under a building foundation.

2. The method of claim 1 wherein the aqueous application of step (c) comprises mixing a pesticide effective against termite infestation with the filtered gray water and injecting said mixture into the subsoil under a building foundation.

3. The method of claim 1 wherein said aqueous application of step (c) comprises utilizing the gray water to irrigate landscape, said gray water is mixed with a fertilizer prior to use in irrigation.

4. The method of claim 1 wherein said aqueous application of step (c) comprises utilizing the gray water to irrigate landscape, said gray water is mixed with a pesticide prior to use in irrigation.

5. The method of claim 1 wherein said aqueous application of step (c) comprises utilizing the gray water to irrigate landscape, said gray water is mixed with a fungicide prior to use in irrigation.

6. A method for maintaining a constant subsoil moisture level under building foundations comprising the steps of:
   (a) monitoring said moisture level;
   (b) injecting gray water into said subsoil when the monitored moisture level drops below a predetermined level.

7. The method of claim 6 further comprising mixing a pesticide with the gray water prior to injection of the gray water into said subsoil, wherein said pesticide is effective against termites.

8. An apparatus for recycling gray water comprising:
   a gray water source;

a filter for removing particles and solids from said gray water source;

a tank for storing the filtered gray water;

a pump for pressurizing said stored gray water;

a means for injecting water-soluble additives into the pressurized gray water; and an osmosis irrigation system routed under a building foundation for dispersal of the pressurized gray water and additive mixture.

9. The apparatus of claim 8 further comprising a means for monitoring the moisture level of the subsoil under the building foundation and metering the injection of the gray water into said subsoil in order to maintain a constant subsoil moisture level.

10. The apparatus of claim 9 wherein said means for monitoring the moisture level is electrically connected to said pump.

11. The apparatus of claim 8 wherein the additive is a pesticide.

12. The apparatus of claim 8 wherein the additive is a fertilizer.

13. The apparatus of claim 8 wherein the additive is a fungicide.

14. The apparatus of claim 8 wherein the additive is suitable for the treatment of termites and ants.

* * * * *